United States Patent [19]

de Toledo et al.

[11] Patent Number: 5,785,689
[45] Date of Patent: Jul. 28, 1998

[54] ENDOSCOPIC CATHETER SHEATH POSITION CONTROL

[75] Inventors: Fernando Alvarez de Toledo, Concord; Thomas H. Doucette, Stow, both of Mass.

[73] Assignee: ACT Medical, Inc., Newton, Mass.

[21] Appl. No.: 683,189

[22] Filed: Jul. 18, 1996

[51] Int. Cl.$^6$ .................................................. A61M 5/178
[52] U.S. Cl. ........................................ 604/165; 604/158
[58] Field of Search ............................... 604/158, 160, 604/162, 165, 166, 171, 282, 164

[56] References Cited

U.S. PATENT DOCUMENTS

| | | | |
|---|---|---|---|
| 3,659,610 | 5/1972 | Cimber | 604/158 X |
| 3,769,975 | 11/1973 | Nimoy et al. | 604/165 |
| 4,222,380 | 9/1980 | Terayama | 128/216 |
| 4,257,419 | 3/1981 | Göltner et al. | 128/303 |
| 4,326,519 | 4/1982 | D'Alo et al. | 604/165 |
| 4,368,730 | 1/1983 | Sharrock | 604/158 |
| 4,610,671 | 9/1986 | Luther | 604/168 |
| 4,735,194 | 4/1988 | Steigmann | 128/6 |
| 4,735,619 | 4/1988 | Sperry et al. | 604/208 |
| 4,795,438 | 1/1989 | Kensey et al. | 604/22 |
| 4,874,376 | 10/1989 | Hawkins, Jr. | 604/165 |
| 4,932,959 | 6/1990 | Horzewski et al. | 604/165 X |
| 4,988,339 | 1/1991 | Vadher | 604/197 |
| 5,009,642 | 4/1991 | Sahi | 604/158 |
| 5,022,399 | 6/1991 | Biegeleisen | 128/622.06 |
| 5,041,124 | 8/1991 | Kensey | 606/170 |
| 5,047,013 | 9/1991 | Rossdeutscher | 604/53 |
| 5,129,884 | 7/1992 | Dysarz | 604/164 |
| 5,219,339 | 6/1993 | Saito | 604/198 |
| 5,226,884 | 7/1993 | Murphy | 604/110 |
| 5,269,789 | 12/1993 | Chin et al. | 606/140 |
| 5,279,590 | 1/1994 | Sinko et al. | 604/263 |
| 5,290,241 | 3/1994 | Kraus et al. | 604/158 X |
| 5,312,375 | 5/1994 | Gurmarnik | 604/158 X |
| 5,354,279 | 10/1994 | Höfling | 604/164 |
| 5,356,416 | 10/1994 | Chu et al. | 606/140 |
| 5,376,075 | 12/1994 | Haughton et al. | 604/171 X |
| 5,380,292 | 1/1995 | Wilson | 604/164 |
| 5,407,431 | 4/1995 | Botich et al. | 604/110 |
| 5,409,012 | 4/1995 | Sahatjian | 128/749 |
| 5,439,455 | 8/1995 | Kieturakis et al. | 604/264 |
| 5,607,407 | 3/1997 | Tolkoff et al. | 604/282 |

FOREIGN PATENT DOCUMENTS

| | | | |
|---|---|---|---|
| 409057A1 | 1/1991 | European Pat. Off. | A61M 5/158 |
| 9528979 | 11/1995 | WIPO | A61M 5/158 |

*Primary Examiner*—Sam Rimell
*Attorney, Agent, or Firm*—Theresa A. Lober

[57] ABSTRACT

An endoscopic catheter distal end position control that enables precise control of distal catheter sheath ends relative to each other while accommodating the long length and flexibility of typical catheters and proximal, remote hand-operable control mechanisms. In a catheter assembly employing this control, an elongated flexible tubular sheath is provided having a distal end and a proximal end. A distal end member is internal to the sheath; this end member is reciprocally axially moveable relative to the sheath distal end between a retracted position that is proximal of the sheath distal end and an extended position in which the end member protrudes beyond the sheath distal end. An elongated end member interconnector is provided, with a distal end of the interconnector being connected to the end member and a proximal end of the interconnector being connected to a position actuator for axially reciprocating the end member relative to the distal end of the sheath. A distal end position controller is located at a point along the sheath to cooperate with the interconnector in limiting the extent of axial retraction of the end member relative to the sheath distal end. A flow channel that extends axially through the end position controller is internal to the sheath and external to the interconnector.

17 Claims, 3 Drawing Sheets

ENDOSCOPIC CATHETER SHEATH POSITION CONTROL

FIELD OF THE INVENTION

This invention relates to endoscopic catheters, and more particularly relates to catheters equipped to accomplish a therapeutic procedure at an internal site such as a gastrointestinal site.

BACKGROUND OF THE INVENTION

Endoscopic catheters are employed for accomplishing a variety of internal therapeutic procedures, for example, for enabling injection therapy at a site of bleeding in the digestive system. Typically, a catheter equipped for such injection therapy includes a needle at the distal end of an injection sheath through which liquid therapeutic injection media is channeled to the needle. An outer sheath over the injection sheath is also typically included to provide both a passageway for irrigation fluid around the needle and a protective encasement for the needle as the distal end of the catheter is moved to the therapy site. Endoscopic catheters equipped for other applications, e.g., delivery of a mechanical vasoconstrictor to an internal site, similarly generally include a mechanical feature at the distal end of an inner sheath that is encased in an outer sheath. Many endoscopic therapeutic procedures are directed to deep internal sites that require an appropriately equipped catheter to be of substantial length, e.g., greater than about one or two meters, to reach the site of interest through, e.g., an endoscope, and further require flexibility in the catheter sheaths for ease of conformance to curves in internal cavities as the catheter is advanced to the intended internal site.

Conventionally, the position of the distal end of an inner catheter sheath and its distal end element, e.g., a needle, is controlled with respect to the outer catheter sheath by way of a remote hand-operable control mechanism at the catheter proximal end opposite the distal end element. For example, as the needle on a catheter is advanced to its intended site, either the injection sheath or outer catheter sheath is typically controlled by hand outside the endoscope to shield the needle from the internal cavity; once the intended site is reached, the needle is then forwardly advanced out the distal end of the outer sheath.

However, the long length and flexibility generally required of catheter sheaths result in only imprecise control of the distal ends of the sheaths using a hand-operable proximal control, however. In particular, it is difficult to achieve precise positioning of the distal end of one sheath with respect to the other using a control mechanism located remotely, at least one meter away, at the opposite, proximal ends of the sheaths, and this limitation is exacerbated by the unpredictable friction between and along the flexible sheaths. Yet the nature of endoscopic therapies typically requires that the distal ends of the sheaths not be rigidly fixed with respect to each other. As a result, the effectiveness of endoscopic therapeutic procedures can be compromised due to ineffective position control of catheter sheath distal ends.

SUMMARY OF THE INVENTION

The invention provides an endoscopic catheter position control that enables precise control of distal catheter sheath ends relative to each other while accommodating the long length and flexibility of typical catheters and proximal, remote hand-operable control mechanisms.

Accordingly, in one aspect, the invention provides a catheter assembly that includes an elongated flexible tubular sheath having a distal end and a proximal end. A distal end member is internal to the sheath; this end member is reciprocally axially moveable relative to the sheath distal end between a retracted position that is proximal of the sheath distal end and an extended position in which the end member protrudes beyond the sheath distal end. An elongated end member interconnector is provided, with a distal end of the interconnector being connected to the end member and a proximal end of the interconnector being connected to a position actuator for axially reciprocating the end member relative to the distal end of the sheath. A distal end position controller is located at a point along the sheath to cooperate with the interconnector in limiting the extent of axial retraction of the end member relative to the sheath distal end. A flow channel that extends axially through the end position controller is internal to the sheath and external to the interconnector.

With this catheter assembly configuration, irrigation or other fluid can be delivered through the outer sheath in the conventional manner with the inner interconnector and distal end member in a fully-retracted position. Unobstruction of the outer sheath fluid communication path provides a superior advantage in that it does not require the addition of an auxiliary or additional fluid communication path beyond the conventional path.

In one embodiment provided by the invention, the end position controller is located at a relatively distal position along the tubular sheath and is embodied as at least one indentation in the sheath that has an inner diameter that is less than an outer diameter of the interconnector at at least one point along the interconnector. Here the interconnector can include a connector that has an outer diameter that is greater than the inner diameter of the indentation. The connector enables connection of the distal end member to the interconnector. Preferably, a plurality of indentations are provided in the sheath, with each indentation being circumferentially separated from adjacent indentations by a flow channel.

In other embodiments, the tubular sheath is a polytetrafluoroethylene sheath and further, the interconnector is a flexible tubular inner sheath. Here the end member can be embodied as a needle cannula connected to the inner sheath, with a connector connecting the needle cannula to the inner sheath.

In another aspect, the invention provides an injection catheter assembly including an elongated, flexible, tubular sheath having a distal end and a proximal end. A needle cannula is internal to the sheath and includes a needle tip that is reciprocally axially moveable relative to the distal end of the sheath between a retracted position in which the sheath covers the needle tip and an extended position in which the needle tip protrudes beyond the sheath distal end. An elongated flexible tube internal to the sheath is connected at its distal end by a needle connector to the needle cannula, and is connected at its proximal end to a position actuator for axially reciprocating the needle tip relative to the sheath distal end. A distal end position controller is located at a point along the sheath to cooperate with the needle connector in limiting the extent of axial retraction of the needle tip relative to the sheath distal end.

Preferably, the tubular sheath and the flexible tube each provide a continuous fluid transmission path between the corresponding sheath and tube distal and proximal ends. The end position controller is in one embodiment located at a relatively distal position along the sheath, preferably corresponding to a fully-retracted needle tip position.

In a further aspect, the invention provides a syringe having a barrel with a distal end and a proximal end. A needle cannula is located internal to the barrel and is reciprocally axially moveable relative to the barrel distal end between a retracted position proximal of the barrel distal end in which the barrel covers the needle tip and an extended position in which the needle tip protrudes beyond the barrel distal end. A needle plunger rod is internal to the barrel; the rod is connected at its distal end to the needle cannula and is connected at its proximal end to a position actuator for axially reciprocating the needle tip relative to the barrel distal end. A distal end position controller is located at a point along the barrel to cooperate with the plunger rod in limiting the extent of axial retraction of the needle tip relative to the barrel distal end. The location of the controller corresponds to the fully retracted needle tip position. Preferably, the plunger rod is connected to the needle by a needle connector, and the position controller preferably is embodied as at least one indentation in the barrel at a point at which retraction of the needle connector to the indentation indicates that the needle cannula tip is fully retracted within the barrel.

The position control of the invention facilitates effective and reliable hand-operable remote control of catheter and syringe distal end members with a mechanism that can be located locally to the distal end but that does not itself require external control; i.e., it provides automatic position control. This control can be applied to a wide range of catheter and syringe configurations where only remote active control of distal end elements can be relied upon during a therapeutic procedure. Other features and advantages of the invention will be apparent from the claims, and from the following description and accompanying drawings.

DESCRIPTION OF A PREFERRED EMBODIMENT

Figure 1:
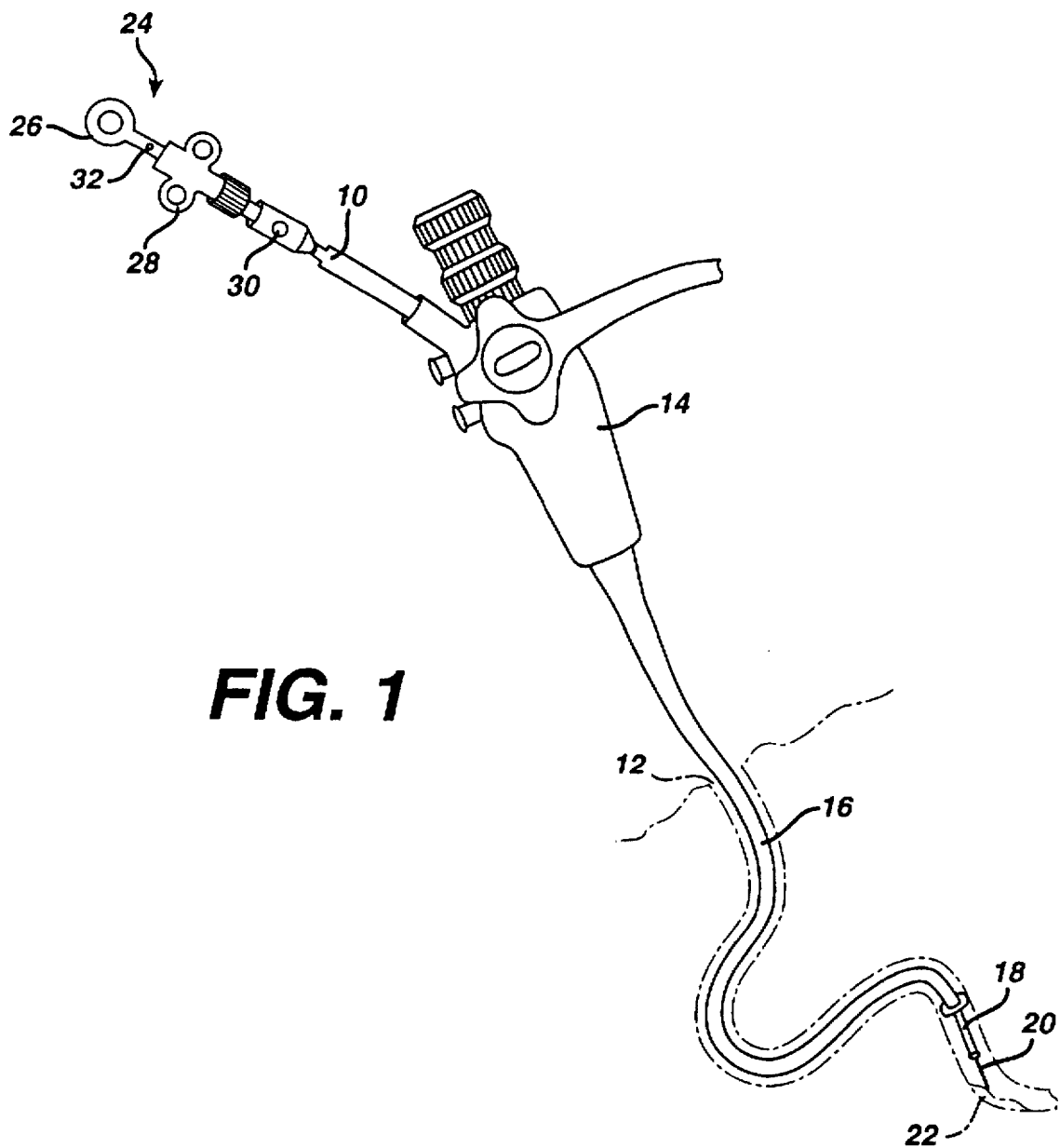
FIG. 1 is a schematic view of an example catheter to which catheter sheath position control can be applied in accordance with the invention, positioned inside an endoscope.

Referring to FIG. 1, there is shown an example endoscopic catheter 10 for which the position control of the invention enables effective control of the relative positions of inner and outer catheter sheaths. The catheter 10 is shown inserted into an internal cavity through an endoscope 14. The endoscope is of a conventional configuration and includes a flexible hollow tube 16 for advancement through an internal cavity 12. The catheter 10 includes an outer sheath 18 and generally coaxial inner sheath (not shown), which are together advanced through the internal cavity through the endoscope hollow tube. The inner sheath is equipped with a distal end mechanism, such as a needle 20, that can be advanced forwardly beyond the distal end of the outer sheath 18 for therapeutically treating an internal site 22 along the cavity. End mechanisms other than needles, e.g., forceps, equipped on either or both the outer or inner catheter sheaths, can also be employed, as will be readily recognized.

As is conventional, the endoscope tube and catheter outer and inner sheaths are formed of a flexible, durable material such as medical grade polytetrafluoroethylene (PTFE). The PTFE tubing can be easily advanced around curves in internal cavities and is substantially impervious to and compatible with both therapeutic and bodily fluids. Typically, the PTFE tube and sheaths are at least about two meters in length, whereby even relatively deep internal sites can be reached.

Also as conventional, the catheter 10 includes a hand control 24 including, e.g., a thumb ring 26 and finger grips 28 that cooperate to enable manual control of the distal ends of the catheter sheaths as the catheter is advanced through the endoscope in the internal cavity. In operation, the thumb ring 26 is first fully retracted from the finger grips 28; this retracted handle position corresponds to full retraction of the catheter inner sheath and its distal end member, e.g., a needle, into the catheter outer sheath. The catheter is then advanced through the endoscope to the intended internal site, optimally with the catheter needle remaining fully retracted.

Once the intended internal site is reached by the distal end of the catheter, irrigation of the site is then typically accomplished by way of the outer sheath; here, an irrigation port 30 in the hand control 24 is employed to introduce, e.g., a flushing fluid to the internal site prior to the start of a therapeutic procedure. The needle or other distal end member on the inner catheter sheath is maintained in a fully- or at least partially-retracted position during this irrigation. The irrigation fluid thereby flows around the inner sheath and needle in the outer sheath as it is delivered to the site.

After sufficient irrigation, the needle or other distal end member is then actuated or deployed to accomplish a procedure such as injection therapy at the intended site. This deployment is enabled by actuating the thumb ring 26 toward the finger grips 28, whereby the tip of the needle is positioned beyond the distal end of the catheter outer sheath, as shown in the figure. In the case of injection therapy, the injection agent can be delivered to the needle through the inner sheath by way of an injection port 32 in the hand control 24. The dual, isolated irrigation-injection fluid communication with the internal site is commonly required to effectively accomplish a desired therapy, and is well-enabled by the generally coaxial dual sheath configuration of the catheter, in combination with needle deployment control.

Upon completion of the therapy, the needle or other distal end member of the catheter inner sheath is fully retracted into the outer sheath by fully actuating the thumb mechanism away from the finger grips in the hand control. The distal end of the catheter can then be moved to other internal sites for additional therapeutic procedures, or can be fully withdrawn from the endoscope.

Figure 2A:
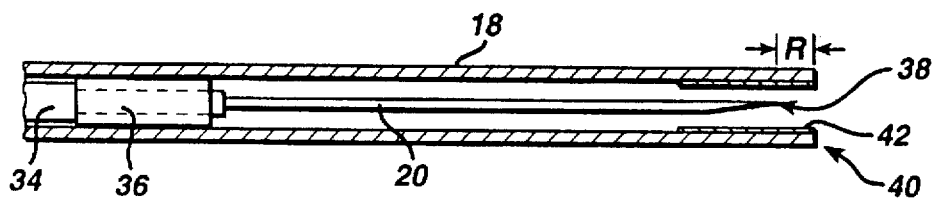
FIGS. 2A and 2B are axial-sectional views of an optimal needle retraction position and needle extension position, respectively, for a prior art catheter equipped to accomplish remote internal injection therapy.
Figure 2B:
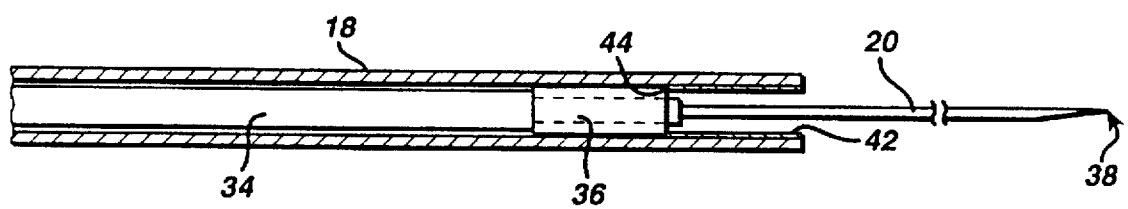

Referring also to FIGS. 2A and 2B, there are shown cross-sections of the catheter with a catheter needle distal end member shown in optimal retracted and extended positions, respectively. Here the catheter inner sheath 34 is explicitly shown connected to the needle 20 by way of a connector, e.g., a crimp ring 36. When the catheter hand control is actuated to correspond to a fully-retracted needle position, the tip 38 of the needle is preferably retracted into the outer sheath 18 by an a priori retraction distance, R.

The retraction distance, R, is preferably sufficient to ensure that the needle tip cannot be exposed as the distal end of the catheter is forwardly advanced through an internal cavity. In this retracted configuration, irrigation or other fluid introduced to the proximal end of the outer sheath flows through the outer sheath and axially around the inner sheath 34, crimp ring 36, and needle 20 to be delivered at the distal end 40 of the outer sheath.

As shown in the FIGS. 2A and 2B, the catheter outer sheath includes a distal end guard 42 secured at the distal end 40 of the outer sheath. Such a guard is typically formed of, e.g., a length of stainless steel tubing that is swaged inside the outer sheath. When the catheter hand control is actuated to correspond to a fully-extended needle position, the inner sheath 34 is forwardly advanced through the outer sheath 18 to extend the needle tip 38 beyond the distal end 40 of the outer sheath. This extension is limited by the distal end guard 42; the inner diameter of the guard is less than the outer diameter of the crimp ring 36, whereby the crimp ring forward travel is stopped at the rear end 44 of the distal end guard 42. In the extended configuration, the intended therapeutic procedure can be accomplished, after which the needle is preferably retracted to its protected position as shown in FIG. 2A. During the procedure, the end guard ensures that the needle or other catheter distal end member does not extend beyond an a priori safe distance corresponding to the given procedure.

In practice, one cannot normally guarantee that the optimal retraction and extension configurations of FIG. 2 are achievable during an endoscopic therapeutic procedure. This is due to both manufacturing and operational factors. After manufacture, the inner and outer catheter sheaths are typically positioned with the inner sheath and distal end member, such as a needle, in a retracted position and are sterilized by way of a heating process, during which the sheaths expand and then later contract during cooling. The catheter is commonly shipped and stored prior to use in a coiled configuration. Due to the occurrence of friction, differential expansion, contraction, and axial movement of the two catheter sheaths during these processes and configurations, the distal end of the inner sheath may not be located in an expected axial position with respect to the outer sheath.

Figure 3A:
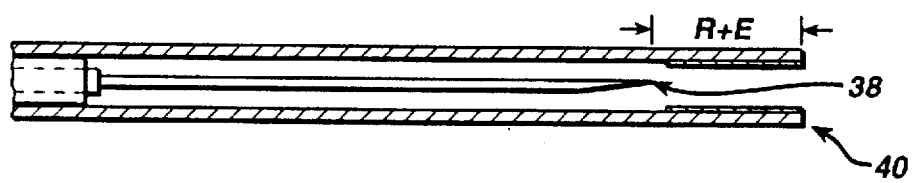
FIG. 3A is an axial-sectional view of a prior art catheter needle that is over-retracted into an outer catheter sheath.

For example, as shown in FIG. 3A, at the start of a therapeutic procedure, the tip 30 of a forward end needle might be retracted from the distal end 40 of the outer sheath by a distance greater than the intended retraction distance, R, instead being retracted an additional error distance, E. Beyond manufacturing and storage factors, the unpredictable friction between the inner and outer sheaths as the catheter is advanced through an endoscope also contribute to the error distance. Indeed, the stretchable, flexible nature of the PTFE sheaths inherently results in unpredictable relative movement of the two sheaths as the outer sheath brushes against the endoscope tube while being advanced through the tube along curves in an internal cavity; commonly, very tight inner cavity angles must be navigated.

Figure 3B:
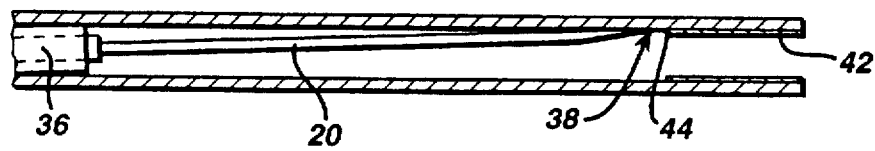
FIG. 3B is an axial-sectional view of a prior art catheter needle that has become lodged behind a catheter end guard.

As shown in FIG. 3B, when the needle tip is retracted beyond the extended retraction distance, R, to a point behind the proximal end 44 of the distal end guard 42, the needle tip 38 can become lodged behind this end 44 of the guard due to radial excursions of the inner sheath, crimp ring 36, and needle 20 as the sheaths are forwardly advanced along curves in an endoscope tube. If such needle lodging occurs, no amount of coaxing by the catheter hand control can generally be expected to dislodge the needle tip because the hand control is at this point already in its fully-retracted position. This over-retraction condition therefore typically requires complete removal of the catheter and use of a new catheter, whereby both equipment and time is lost.

Figure 3C:
FIG. 3C is an axial-sectional view of a prior art catheter needle that has pierced an outer catheter sheath.

In yet a more serious over-retraction condition, as shown in FIG. 3C, the needle tip 38 can actually pierce the outer sheath 38, thereby extending beyond the catheter. In this configuration, the endoscope tube can also be pierced and/or serious trauma can occur as the catheter is advanced through the endoscope along an internal cavity; as mentioned earlier, internal cavities often present quite tight angles, thereby exaggerating the potential for this to occur. As can be readily understood, the potential for occurrence of this over-retraction condition is a serious concern for and limitation of typical catheters.

But even if the specific over-retraction conditions illustrated in FIGS. 3B–3C do not occur during use of a catheter, effective accomplishment of a therapeutic procedure with the catheter can still be inhibited. In particular, given even a benign over-retraction condition, full extension of the catheter hand control can in some cases not produce adequate deployment of the inner sheath needle or other distal end member. Because endoscopic therapeutic procedures such as endoscopic injection therapy require a relatively precise amount of extension for, e.g., enabling effective tissue injection, such inadequate deployment is often unacceptable. But the full stroke of catheter hand control actuation can not be relied upon to in all cases overcome the entire extent of over-retraction, due to the wide dimensional tolerances of the catheter sheaths along their substantial lengths. Indeed, over-retraction may be of such a degree that the catheter needle does not at all extend beyond the distal end of the catheter outer sheath even when the hand-control is fully extended.

The lack of certainty associated with retraction and extension of the distal end member of an endoscopic catheter has generally led to a requirement for relatively explicit instructions and warnings as to possible failure conditions to which one must be constantly alert during a therapeutic procedure. It has also generally required that several catheters be readily available at the time of a procedure to enable completion of the procedure even in the face of an uncompromising over-retraction condition.

Figure 4A:
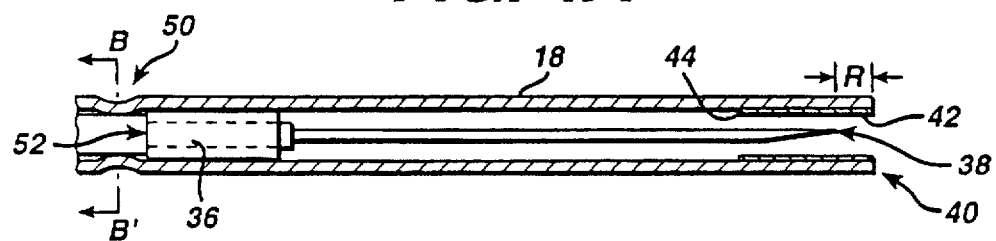
FIG. 4A is an axial-sectional view of a catheter employing the sheath position control of the invention to enable optimal needle retraction position.
Figure 4B:
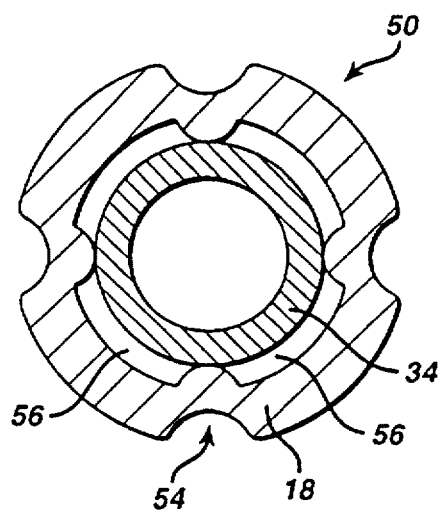
FIG. 4B is a cross-sectional view of the catheter of FIG. 4A, taken along B–B'.
Figure 4C:
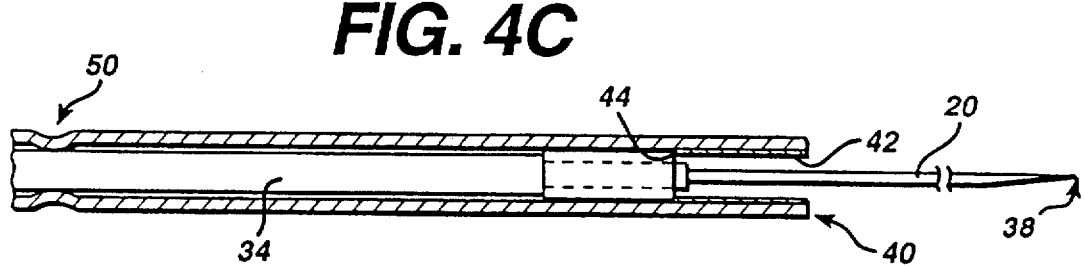
FIG. 4C is an axial-sectional view of a catheter employing the sheath position control of the invention to enable optimal needle extension position.

Turning now to FIGS. 4A–4C there is shown the catheter sheath position control provided by the invention for overcoming the conventional catheter failure mechanisms described above. In general, the sheath position control 50 includes one or more geometric features, at one or more locations along the catheter, that limit the retraction range of the inner catheter sheath and its distal end member while accommodating the dual fluid communication channels provided by the inner and outer sheaths In a first example sheath position control in accordance with the invention, as shown in FIG. 4, the outer sheath 18 is provided with one or more limited indentations 54 that result in a discontinuous radial profile of the outer sheath at the location of the one or more indentations. The inner diameter of each such indentation is less than the outer diameter of one or more features on the inner sheath, e.g., the crimp ring securing the needle to the inner sheath. With this configuration, the indentations limit retraction of the rear face 52 of the crimp ring 36 to only the location of the indentations. Accordingly, it is preferred that the one or more indentations be located along the outer sheath at a point or points such that full retraction of the catheter hand control and corresponding retraction of the crimp ring, or other inner sheath feature, to the indentations results in a desired a priori retraction distance, R, of the needle tip 38 from the distal end 40 of the outer sheath, with R, preferably corresponding to a fully-retracted needle tip, i.e., needle tip that is safely within the outer sheath.

It is further preferred that the indentation location correspond to a retraction distance, R, that is less than the extent of the proximal end 44 of the distal end guard 42. With this configuration, the sheath position control 50 enables control of the inner sheath and its distal end member such that the end member cannot become lodged behind the guard or pierce through the outer sheath at points proximal of the guard. By restricting the allowable axial range of the tip of the needle or other distal end member to only the extent of the proximal end of the guard, the failure mechanisms commonly associated with conventional catheters are significantly inhibited.

As shown in FIG. 4B, the sheath position control indentations 54 are not continuous around the circumference of the outer sheath. Adjacent each indentation are flow channels 56. These channels are each preferably of at least a minimum cross-sectional area that allows fluid to flow through the channel. Irrigation or other fluid can then be delivered through the outer sheath in the conventional manner with the inner sheath and needle or other distal end member in a fully-retracted position. Fluid can thus pass freely around the inner sheath with minimal resistance. Unobstruction of the outer sheath fluid communication path provides a superior advantage in that it does not require the addition of an auxiliary or additional fluid communication path beyond the conventional path.

While four sheath position control indentations 54 are shown in FIG. 4B, it is to be recognized that any reasonable number could be employed, depending on a given catheter design application and requirement. The use of such indentations is particularly advantageous in that the indentations can be very easily manufactured. A conventional crimping tool can be used to apply the desired number of indentations at an intended location or locations, without the need for additional materials or separate parts. The resulting indentations retain the flexibility of the outer sheath such that the catheter retains its ability to be advanced through tightly-curved interior cavities. This crimping technique is based on the use of a sheath material that can retain a crimp indentation once it is impressed on the sheath, and thus such a material, e.g., PTFE, is preferred for the outer sheath.

The sheath position control of the invention can be embodied in other manners, however. For example, a sleeve, band, ligature, or ring can be placed externally around the outer sheath at a desired location or locations to impress and maintain one or more indentations in the outer sheath. Alternatively, a sleeve or ring can be secured internally to the outer sheath at a desired location to itself act as the position control feature. Other such position control features are contemplated by the invention. For example, one or more protrusions, sleeves, bands, or rings can be placed externally around the inner sheath internal to the outer sheath at a desired location or locations to cooperate with one or more outer sheath features. Whatever position control is used, if the outer sheath is to be employed for providing a fluid communication path to or from the internal therapeutic site, it is preferred that the position control feature or features embody a nonuniform radial profile such that flow channels between the outer sheath and inner sheath are provided.

As shown in FIG. 4C, the sheath position control 50 of the invention enables reliable and effective forward extension of the inner sheath 34 and needle 20 all the way to the proximal end 44 of the distal end guard 42. During manufacture or use, the inner sheath and needle can not retract further than the position control 50, whereby full extension of the catheter hand control results in a corresponding full extension of the inner sheath and needle. If during manufacture or use the inner sheath and needle advance slightly ahead of the position control 50, the end guard 42 ensures that the needle does not extend beyond its intended range when the hand control extension is actuated.

The catheter sheath position control of the invention thereby facilitates effective and reliable hand-operable remote control of catheter sheath distal end positions with a mechanism located locally to the distal ends but that does not itself require external control; i.e., it provides automatic sheath position control. This control can be applied to a wide range of catheter configurations where only remote active control of distal end elements can be relied upon during a therapeutic or other internal procedure. For example, a catheter equipped to enable remote internal injection or other mechanical procedure through a gastroscope or other elongated advanceable scope can be addressed by the sheath position control to enable accurate catheter positioning in a gastrointestinal tract or other cavity.

Indeed, distal end position control can be established on most any catheter-based device through use of the invention position control. For example, the distal end member to be controlled need not be connected to a tubular inner sheath; a guidewire, rod, or other elongated end member interconnector, whether flexible or rigid, can be accommodated by the position control. The interconnector need not be coaxially aligned with the outer sheath, but must provide a cooperative configuration for enabling position control of a distal end member. A double outer sheath configured with a plurality of end members and end member interconnectors can also be accommodated.

Hypodermic needle configurations, both elongated and relatively short, can likewise achieve remote distal end position control of the needle tip by way of the invention position control. Such control can be advantageous, e.g., for providing a positive indicator of full retraction of a needle tip once an injection process is completed.

It is recognized, of course, that those skilled in the art may make other various modifications and additions to the embodiments of the position control described above without departing from the spirit and scope of the present contribution to the art. Accordingly, it is to be understood that the protection sought to be afforded hereby should be deemed to extend to the subject matter claims and all equivalents thereof fairly within the scope of the invention.

We claim:

1. A catheter assembly comprising:
   an elongated, flexible, tubular sheath having a distal end and a proximal end;
   a distal end member internal to the sheath and reciprocally axially moveable relative to the sheath distal end between a retracted position proximal of the sheath distal end and an extended position in which the end member protrudes beyond the sheath distal end;

an elongated end member interconnector having a distal end and a proximal end, the interconnector distal end being connected to the end member and the interconnector proximal end being connected to a position actuator for axially reciprocating the end member relative to the sheath distal end;

a self acting distal end position controller located at a point along the sheath to self-actively cooperate with the end member interconnector in limiting the extent of axial retraction of the end member relative to the sheath distal end; and a flow channel internal to the sheath and external to the end member interconnector, the flow channel extending axially through the distal end position controller.

2. The catheter assembly of claim 1 wherein the distal end position controller is located at a relatively distal position along the sheath.

3. The catheter assembly of claim 2 wherein the distal end position controller comprises at least one indentation in the sheath, the at least one indentation having an inner diameter that is less than an outer diameter of the end member interconnector at at least one point along the interconnector.

4. The catheter assembly of claim 3 wherein the distal end of the end member interconnector comprises a connector, the connector having an outer diameter that is greater than the inner diameter of the at least one indentation and connecting the interconnector to the end member.

5. The catheter assembly of claim 3 wherein the at least one indentation comprises a plurality of indentations each circumferentially separated from adjacent indentations by a flow channel.

6. The catheter assembly of claim 3 wherein the sheath comprises a polytetrafluoroethylene sheath.

7. The catheter assembly of claim 1 wherein the end member interconnector comprises a flexible tubular inner sheath.

8. The catheter assembly of claim 7 wherein the end member comprises a needle cannula connected to the inner sheath.

9. The catheter assembly of claim 8 further comprising a connector connecting the needle cannula to the inner sheath.

10. An injection catheter assembly comprising:

an elongated, flexible, tubular sheath having a distal end and a proximal end;

a needle cannula internal to the sheath and having a distal tip, the needle cannula tip being reciprocally axially moveable relative the sheath distal end between a retracted position proximal of the sheath distal end whereby the sheath covers the needle tip and an extended position whereby the needle tip protrudes beyond the sheath distal end;

an elongated, flexible tube internal to the sheath and having a distal end and a proximal end, the tube distal end being connected to the needle cannula by a needle connector and the tube proximal end being connected to a position actuator for axially reciprocating the needle tip relative to the sheath distal end; and a self acting distal end position controller located at a point along the sheath to self actively cooperate with the needle connector in limiting the extent of axial retraction of the needle tip relative to the sheath distal end.

11. The injection catheter assembly of claim 10 wherein the tubular sheath and the tube each provide a continuous fluid transmission path between the corresponding distal end and proximal end.

12. The catheter assembly of claim 10 wherein the distal end position controller is located at a relatively distal position along the sheath.

13. The catheter assembly of claim 12 wherein the location of the distal end position controller corresponds to a fully-retracted needle tip position.

14. The injection catheter assembly of claim 11 wherein the distal end position controller comprises at least one indentation in the tubular sheath, the at least one indentation having an inner diameter that is less than an outer diameter of the needle connector.

15. The injection catheter assembly of claim 14 wherein the at least one indentation comprises a plurality of indentations each circumferentially separated from adjacent indentations by a flow channel.

16. A syringe comprising:

a barrel having a distal end and a proximal end;

a needle cannula having a distal tip, the needle cannula tip being located internal to the barrel and being reciprocally axially moveable relative to the barrel distal end between a retracted position proximal of the barrel distal end whereby the barrel covers the needle tip and an extended position whereby the needle tip protrudes beyond the barrel distal end;

a needle plunger rod internal to the barrel and having a distal end and a proximal end, the rod distal end being connected to the needle cannula and the rod proximal end being connected to a position actuator for axially reciprocating the needle tip relative to the barrel distal end; and a self acting distal end position controller located at a point along the barrel to self actively cooperate with the plunger rod in limiting the extent of axial retraction of the needle tip relative to the barrel distal end, the location of the controller corresponding to a fully retracted needle tip position.

17. The syringe of claim 16 further comprising a needle connector connecting the plunger rod to the needle, and wherein the distal end position controller comprises at least one indentation in the barrel located at a point at which retraction of the needle connector to the at least one indentation indicates that the needle cannula tip is fully retracted within the barrel.

* * * * *

UNITED STATES PATENT AND TRADEMARK OFFICE
CERTIFICATE OF CORRECTION

PATENT NO : 5,785,689
DATED : July 28, 1998
INVENTOR(S): Fernando Alvarez de Toledo and Thomas H. Doucette It is certified that error appears in the above-identified patent and that said Letters Patent is hereby corrected as shown below:

At Item 19 on the cover page, the name "de Toledo"
should read --Alvarez de Toledo--.

Signed and Sealed this

Twenty-fourth Day of November, 1998

Attest:

BRUCE LEHMAN

*Attesting Officer*  *Commissioner of Patents and Trademarks*